United States Patent
Blum et al.

(10) Patent No.: US 12,235,524 B2
(45) Date of Patent: Feb. 25, 2025

(54) FLEXIBLE ELECTRO-ACTIVE LENS

(71) Applicant: e-Vision Smart Optics, Inc., Sarasota, FL (US)

(72) Inventors: Ronald D. Blum, Roanoke, VA (US); Joshua N. Haddock, Roanoke, VA (US); William Kokonaski, Gig Harbor, WA (US); John D. Hunkeler, Mission, KS (US)

(73) Assignee: e-Vision Smart Optics, Inc., Sarasota, FL (US)

( * ) Notice: Subject to any disclaimer, the term of this patent is extended or adjusted under 35 U.S.C. 154(b) by 0 days.

(21) Appl. No.: 18/065,720

(22) Filed: Dec. 14, 2022

(65) Prior Publication Data
US 2023/0113330 A1    Apr. 13, 2023

Related U.S. Application Data

(60) Continuation of application No. 17/938,070, filed on Oct. 5, 2022, which is a division of application No.
(Continued)

(51) Int. Cl.
*G02C 7/04* (2006.01)
*A61F 2/14* (2006.01)
(Continued)

(52) U.S. Cl.
CPC .............. *G02C 7/083* (2013.01); *A61F 2/145* (2013.01); *A61F 2/1616* (2013.01); *A61F 2/1627* (2013.01); *G02B 1/043* (2013.01); *G02C 7/04* (2013.01); *G02C 7/049* (2013.01); *A61F 2250/0001* (2013.01); *A61N 1/0543* (2013.01); *G02C 2202/18* (2013.01); *G02C 2202/20* (2013.01)

(58) Field of Classification Search
USPC ...................................................... 351/159.03
See application file for complete search history.

(56) References Cited

U.S. PATENT DOCUMENTS

| | | | |
|---|---|---|---|
| 2,437,642 | A | 3/1948 | Henroteau |
| 2,576,581 | A | 11/1951 | Edwards |

(Continued)

FOREIGN PATENT DOCUMENTS

| | | |
|---|---|---|
| EP | 0154962 A2 | 9/1985 |
| EP | 0233104 A1 | 8/1987 |

(Continued)

OTHER PUBLICATIONS

Notice of Deficiencies in Israel Application No. 296003 mailed May 30, 2023, 8 pages.
(Continued)

*Primary Examiner* — Darryl J Collins
(74) *Attorney, Agent, or Firm* — Smith Baluch LLP

(57) ABSTRACT

A lens including a flexible refractive optic having a fixed refractive index, an electro-active element embedded within the flexible refractive optic, wherein the electro-active element has an alterable refractive index, and a controller electrically connected to the electro-active element wherein when power is applied thereto the refractive index of the electro-active element is altered.

14 Claims, 11 Drawing Sheets

Related U.S. Application Data

16/159,289, filed on Oct. 12, 2018, now Pat. No. 11,474,380, which is a division of application No. 14/850,232, filed on Sep. 10, 2015, now Pat. No. 10,126,569, which is a continuation of application No. 12/017,858, filed on Jan. 22, 2008, now Pat. No. 9,155,614.

(60) Provisional application No. 60/960,607, filed on Oct. 5, 2007, provisional application No. 60/881,514, filed on Jan. 22, 2007.

(51) Int. Cl.
| | |
|---|---|
| A61F 2/16 | (2006.01) |
| G02B 1/04 | (2006.01) |
| G02C 7/02 | (2006.01) |
| G02C 7/08 | (2006.01) |
| A61N 1/05 | (2006.01) |

(56) References Cited

U.S. PATENT DOCUMENTS

| | | |
|---|---|---|
| 3,161,718 A | 12/1964 | De Luca |
| 3,245,315 A | 4/1966 | Marks et al. |
| 3,248,460 A | 4/1966 | Naujokas |
| 3,309,162 A | 3/1967 | Kosanke et al. |
| 3,614,215 A | 10/1971 | Leo |
| 3,738,734 A | 6/1973 | Tait et al. |
| 3,791,719 A | 2/1974 | Kratzer et al. |
| 4,062,629 A | 12/1977 | Winthrop |
| 4,174,156 A | 11/1979 | Glorieux |
| 4,181,408 A | 1/1980 | Senders |
| 4,190,330 A | 2/1980 | Berreman |
| 4,190,621 A | 2/1980 | Greshes |
| 4,264,154 A | 4/1981 | Petersen |
| 4,279,474 A | 7/1981 | Belgorod |
| 4,300,818 A | 11/1981 | Schachar |
| 4,320,939 A | 3/1982 | Mueller |
| 4,373,218 A | 2/1983 | Schachar |
| 4,395,736 A | 7/1983 | Fraleux |
| 4,418,990 A | 12/1983 | Gerber |
| 4,423,929 A | 1/1984 | Gomi |
| 4,457,585 A | 7/1984 | Ducorday |
| 4,461,550 A | 7/1984 | Legendre |
| 4,461,629 A | 7/1984 | Arisaki |
| 4,466,703 A | 8/1984 | Nishimoto |
| 4,466,706 A | 8/1984 | Lamothe, II |
| 4,529,268 A | 7/1985 | Brown |
| 4,564,267 A | 1/1986 | Nishimoto |
| 4,572,616 A | 2/1986 | Kowel et al. |
| 4,577,928 A | 3/1986 | Brown |
| 4,601,545 A | 7/1986 | Kern |
| 4,609,824 A | 9/1986 | Munier et al. |
| 4,709,996 A | 12/1987 | Michelson |
| 4,712,870 A | 12/1987 | Robinson et al. |
| 4,756,605 A | 7/1988 | Okada et al. |
| 4,772,094 A | 9/1988 | Sheiman |
| D298,250 S | 10/1988 | Kildall |
| 4,781,440 A | 11/1988 | Toda |
| 4,787,733 A | 11/1988 | Silva |
| 4,787,903 A | 11/1988 | Grendahl |
| 4,795,248 A | 1/1989 | Okada et al. |
| 4,813,777 A | 3/1989 | Rainville et al. |
| 4,816,031 A | 3/1989 | Pfoff |
| 4,818,095 A | 4/1989 | Takeuchi |
| 4,836,652 A | 6/1989 | Oishi et al. |
| 4,842,400 A | 6/1989 | Klein |
| 4,869,588 A | 9/1989 | Frieder et al. |
| 4,873,029 A | 10/1989 | Blum |
| 4,880,300 A | 11/1989 | Payner et al. |
| 4,890,903 A | 1/1990 | Treisman et al. |
| 4,904,063 A | 2/1990 | Okada et al. |
| 4,907,860 A | 3/1990 | Noble |
| 4,909,626 A | 3/1990 | Purvis et al. |
| 4,919,520 A | 4/1990 | Okada et al. |
| 4,921,728 A | 5/1990 | Takiguchi et al. |
| 4,927,241 A | 5/1990 | Kuijk |
| 4,929,865 A | 5/1990 | Blum |
| 4,930,884 A | 6/1990 | Tichenor et al. |
| 4,944,584 A | 7/1990 | Maeda et al. |
| 4,945,242 A | 7/1990 | Berger et al. |
| 4,952,048 A | 8/1990 | Frieder et al. |
| 4,952,788 A | 8/1990 | Berger et al. |
| 4,955,712 A | 9/1990 | Barth et al. |
| 4,958,907 A | 9/1990 | Davis |
| 4,961,639 A | 10/1990 | Lazarus |
| 4,968,127 A | 11/1990 | Russell et al. |
| 4,981,342 A | 1/1991 | Fiala |
| 4,991,951 A | 2/1991 | Mizuno et al. |
| 5,015,086 A | 5/1991 | Okaue et al. |
| 5,030,882 A | 7/1991 | Solero |
| 5,050,981 A | 9/1991 | Roffman |
| 5,066,301 A | 11/1991 | Wiley |
| 5,067,795 A | 11/1991 | Senatore |
| 5,073,021 A | 12/1991 | Marron |
| 5,076,665 A | 12/1991 | Petersen |
| 5,089,023 A | 2/1992 | Swanson |
| 5,091,801 A | 2/1992 | Ebstein |
| 5,108,169 A | 4/1992 | Mandell |
| 5,114,628 A | 5/1992 | Hoefer et al. |
| 5,130,856 A | 7/1992 | Tichenor et al. |
| 5,142,411 A | 8/1992 | Fiala |
| 5,147,585 A | 9/1992 | Blum |
| 5,150,234 A | 9/1992 | Takahashi et al. |
| 5,171,266 A | 12/1992 | Wiley et al. |
| 5,173,723 A | 12/1992 | Volk |
| 5,178,800 A | 1/1993 | Blum |
| 5,182,585 A | 1/1993 | Stoner |
| 5,184,156 A | 2/1993 | Black et al. |
| 5,200,859 A | 4/1993 | Payner et al. |
| 5,208,688 A | 5/1993 | Fergason et al. |
| 5,217,490 A | 6/1993 | Sayano et al. |
| 5,219,497 A | 6/1993 | Blum |
| 5,229,797 A | 7/1993 | Futhey et al. |
| 5,229,885 A | 7/1993 | Quaglia |
| 5,231,430 A | 7/1993 | Kohayakawa |
| 5,239,412 A | 8/1993 | Naka et al. |
| D342,063 S | 12/1993 | Howitt et al. |
| 5,305,028 A | 4/1994 | Okano |
| 5,306,926 A | 4/1994 | Yonemoto |
| 5,324,930 A | 6/1994 | Jech |
| D350,342 S | 9/1994 | Sack |
| 5,352,886 A | 10/1994 | Kane |
| 5,359,444 A | 10/1994 | Piosenka et al. |
| 5,375,006 A | 12/1994 | Haas |
| 5,382,986 A | 1/1995 | Black et al. |
| 5,386,308 A | 1/1995 | Michel et al. |
| 5,411,537 A | 5/1995 | Munshi et al. |
| 5,424,927 A | 6/1995 | Schaller et al. |
| 5,440,357 A | 8/1995 | Quaglia |
| 5,443,506 A | 8/1995 | Garabet |
| 5,451,766 A | 9/1995 | Van |
| 5,488,439 A | 1/1996 | Weltmann |
| 5,512,371 A | 4/1996 | Gupta et al. |
| 5,522,323 A | 6/1996 | Richard |
| 5,552,841 A | 9/1996 | Gallorini et al. |
| 5,608,587 A | 3/1997 | Smith |
| 5,615,588 A | 4/1997 | Gottschald |
| 5,628,794 A | 5/1997 | Lindstrom |
| 5,653,751 A | 8/1997 | Samiy et al. |
| 5,654,786 A | 8/1997 | Gerald |
| 5,668,620 A | 9/1997 | Kurtin et al. |
| 5,682,223 A | 10/1997 | Menezes et al. |
| 5,683,457 A | 11/1997 | Gupta et al. |
| RE35,691 E | 12/1997 | Theirl et al. |
| 5,702,819 A | 12/1997 | Gupta et al. |
| 5,712,721 A | 1/1998 | Large |
| 5,728,155 A | 3/1998 | Anello et al. |
| 5,728,156 A | 3/1998 | Gupta et al. |
| 5,739,959 A | 4/1998 | Quaglia |
| 5,757,458 A | 5/1998 | Miller et al. |
| 5,777,719 A | 7/1998 | Williams et al. |
| 5,815,233 A | 9/1998 | Morokawa et al. |

(56) References Cited

U.S. PATENT DOCUMENTS

| | | |
|---|---|---|
| 5,815,239 A | 9/1998 | Chapman et al. |
| 5,859,685 A | 1/1999 | Gupta et al. |
| 5,861,934 A | 1/1999 | Blum et al. |
| 5,861,936 A | 1/1999 | Sorensen |
| 5,877,876 A | 3/1999 | Birdwell |
| 5,900,720 A | 5/1999 | Kallman et al. |
| 5,905,561 A | 5/1999 | Lee et al. |
| 5,949,521 A | 9/1999 | Williams et al. |
| 5,953,098 A | 9/1999 | Lieberman et al. |
| 5,956,183 A | 9/1999 | Epstein et al. |
| 5,963,300 A | 10/1999 | Horwitz |
| 5,971,540 A | 10/1999 | Ofner |
| 5,980,037 A | 11/1999 | Conway |
| 5,999,328 A | 12/1999 | Kurtin et al. |
| 6,040,947 A | 3/2000 | Kurtin et al. |
| 6,050,687 A | 4/2000 | Bille et al. |
| 6,069,742 A | 5/2000 | Silver |
| 6,086,203 A | 7/2000 | Blum et al. |
| 6,086,204 A | 7/2000 | Magnante |
| 6,095,651 A | 8/2000 | Williams et al. |
| 6,099,117 A | 8/2000 | Gregory |
| 6,115,177 A | 9/2000 | Vossler |
| 6,139,148 A | 10/2000 | Menezes |
| 6,145,987 A | 11/2000 | Baude et al. |
| 6,188,525 B1 | 2/2001 | Silver |
| 6,191,881 B1 | 2/2001 | Tajima |
| 6,199,984 B1 | 3/2001 | Menezes |
| 6,199,986 B1 | 3/2001 | Williams et al. |
| 6,213,602 B1 | 4/2001 | Smarto |
| 6,270,220 B1 | 8/2001 | Keren |
| 6,271,915 B1 | 8/2001 | Frey et al. |
| 6,282,449 B1 | 8/2001 | Kamerling et al. |
| 6,299,311 B1 | 10/2001 | Williams et al. |
| 6,305,802 B1 | 10/2001 | Roffman et al. |
| 6,324,429 B1 | 11/2001 | Shire et al. |
| 6,325,508 B1 | 12/2001 | Decreton et al. |
| 6,338,559 B1 | 1/2002 | Williams et al. |
| 6,350,031 B1 | 2/2002 | Lashkari et al. |
| 6,359,674 B1 | 3/2002 | Horiuchi |
| 6,390,623 B1 | 5/2002 | Kokonaski et al. |
| 6,396,622 B1 | 5/2002 | Alden |
| 6,437,762 B1 | 8/2002 | Birdwell |
| 6,437,925 B1 | 8/2002 | Nishioka |
| 6,464,363 B1 | 10/2002 | Nishioka et al. |
| 6,491,394 B1 | 12/2002 | Blum et al. |
| 6,501,443 B1 | 12/2002 | Mcmahon |
| 6,554,425 B1 | 4/2003 | Roffman et al. |
| 6,609,794 B2 | 8/2003 | Levine |
| 6,614,408 B1 | 9/2003 | Mann |
| 6,616,275 B1 | 9/2003 | Dick et al. |
| 6,616,279 B1 | 9/2003 | Davis et al. |
| 6,618,208 B1 | 9/2003 | Silver |
| 6,626,532 B1 | 9/2003 | Nishioka et al. |
| 6,631,001 B2 | 10/2003 | Kuiseko |
| 6,638,304 B2 | 10/2003 | Azar |
| 6,643,552 B2 | 11/2003 | Edell et al. |
| 6,652,096 B1 | 11/2003 | Morris et al. |
| 6,667,471 B2 | 12/2003 | Bos et al. |
| 6,682,195 B2 | 1/2004 | Dreher |
| 6,705,729 B2 | 3/2004 | Piers et al. |
| 6,709,105 B2 | 3/2004 | Menezes |
| 6,709,107 B2 | 3/2004 | Jiang et al. |
| 6,709,108 B2 | 3/2004 | Levine et al. |
| 6,738,199 B2 | 5/2004 | Nishioka |
| 6,768,536 B2 | 7/2004 | Okuwaki et al. |
| 6,774,871 B2 | 8/2004 | Birdwell |
| 6,778,246 B2 | 8/2004 | Sun et al. |
| 6,793,340 B1 | 9/2004 | Morris et al. |
| 6,833,938 B2 | 12/2004 | Nishioka |
| 6,840,619 B2 | 1/2005 | Dreher |
| 6,851,805 B2 | 2/2005 | Blum et al. |
| 6,859,333 B1 | 2/2005 | Ren et al. |
| 6,883,916 B2 | 4/2005 | Menezes |
| 6,886,938 B1 | 5/2005 | Menezes |
| 6,893,124 B1 | 5/2005 | Kurtin |
| 6,894,751 B2 | 5/2005 | Payne et al. |
| 6,902,271 B2 | 6/2005 | Perrott et al. |
| 6,918,570 B2 | 7/2005 | Ahn |
| 6,918,670 B2 | 7/2005 | Blum et al. |
| 6,948,818 B2 | 9/2005 | Williams et al. |
| 6,951,391 B2 | 10/2005 | Michael et al. |
| 6,955,433 B1 | 10/2005 | Benjamin et al. |
| 6,956,682 B2 | 10/2005 | Benjamin |
| 6,976,982 B2 | 12/2005 | Santini et al. |
| 6,986,579 B2 | 1/2006 | Blum et al. |
| 7,008,054 B1 | 3/2006 | Kurtin et al. |
| 7,009,757 B2 | 3/2006 | Nishioka et al. |
| 7,018,040 B2 | 3/2006 | Blum et al. |
| 7,019,890 B2 | 3/2006 | Meredith et al. |
| 7,041,133 B1 | 5/2006 | Azar |
| 7,085,065 B2 | 8/2006 | Silver |
| 7,133,172 B2 | 11/2006 | Nishioka |
| 7,137,702 B2 | 11/2006 | Piers et al. |
| 7,137,952 B2 | 11/2006 | Leonardi et al. |
| 7,159,981 B2 | 1/2007 | Kato |
| 7,159,983 B2 | 1/2007 | Menezes et al. |
| 7,195,353 B2 | 3/2007 | Blum et al. |
| 7,209,097 B2 | 4/2007 | Suyama et al. |
| 7,229,173 B2 | 6/2007 | Menezes |
| 7,261,736 B1 | 8/2007 | Azar |
| 7,289,260 B2 * | 10/2007 | Kaufman .................. G02B 3/14 351/159.05 |
| 8,778,022 B2 | 7/2014 | Blum et al. |
| 9,155,614 B2 | 10/2015 | Blum et al. |
| 9,801,709 B2 | 10/2017 | Blum et al. |
| 10,092,395 B2 | 10/2018 | Blum et al. |
| 10,126,569 B2 | 11/2018 | Blum et al. |
| 10,172,704 B2 | 1/2019 | Blum et al. |
| 10,729,539 B2 | 8/2020 | Blum et al. |
| 10,852,766 B2 | 12/2020 | Blum et al. |
| 11,474,380 B2 | 10/2022 | Blum et al. |
| 2001/0055094 A1 | 12/2001 | Zhang |
| 2002/0140899 A1 | 10/2002 | Blum et al. |
| 2002/0149739 A1 | 10/2002 | Perrott et al. |
| 2002/0186346 A1 | 12/2002 | Stantz et al. |
| 2003/0018383 A1 | 1/2003 | Azar |
| 2003/0060878 A1 | 3/2003 | Shadduck |
| 2003/0112523 A1 | 6/2003 | Daniell |
| 2003/0151721 A1 | 8/2003 | Lai et al. |
| 2003/0199978 A1 | 10/2003 | Lindsey et al. |
| 2003/0208265 A1 | 11/2003 | Ho et al. |
| 2003/0210377 A1 | 11/2003 | Blum et al. |
| 2004/0008319 A1 | 1/2004 | Lai et al. |
| 2004/0010130 A1 | 1/2004 | Katsuki et al. |
| 2004/0027501 A1 | 2/2004 | Blum et al. |
| 2004/0039298 A1 | 2/2004 | Abreu |
| 2004/0108971 A1 | 6/2004 | Waldern et al. |
| 2004/0117011 A1 | 6/2004 | Aharoni et al. |
| 2004/0130677 A1 | 7/2004 | Liang et al. |
| 2004/0179280 A1 | 9/2004 | Nishioka |
| 2004/0196435 A1 | 10/2004 | Dick et al. |
| 2004/0246440 A1 | 12/2004 | Andino et al. |
| 2005/0073739 A1 | 4/2005 | Meredith et al. |
| 2005/0099595 A1 | 5/2005 | Lindacher |
| 2005/0113912 A1 | 5/2005 | Feenstra et al. |
| 2005/0124983 A1 | 6/2005 | Frey et al. |
| 2005/0256571 A1 | 11/2005 | Azar |
| 2006/0044510 A1 | 3/2006 | Williams et al. |
| 2006/0113054 A1 | 6/2006 | Silvestrini |
| 2006/0122531 A1 | 6/2006 | Goodall et al. |
| 2006/0146281 A1 | 7/2006 | Goodall et al. |
| 2006/0164593 A1 | 7/2006 | Peyghambarian et al. |
| 2006/0183986 A1 | 8/2006 | Rice et al. |
| 2007/0153354 A1 | 7/2007 | Duston et al. |
| 2007/0153405 A1 | 7/2007 | Kuiper et al. |
| 2007/0273825 A1 | 11/2007 | Legerton et al. |
| 2010/0002190 A1 | 1/2010 | Clarke et al. |

FOREIGN PATENT DOCUMENTS

| | | |
|---|---|---|
| EP | 0237365 A1 | 9/1987 |
| EP | 0578833 A1 | 1/1994 |
| EP | 0649044 A1 | 4/1995 |
| EP | 0918248 A2 | 5/1999 |

(56) References Cited

FOREIGN PATENT DOCUMENTS

| | | |
|---|---|---|
| GB | 2169417 A | 7/1986 |
| GB | 2170613 A | 8/1986 |
| JP | S5576323 A | 6/1980 |
| JP | S61156227 A | 7/1986 |
| JP | S61502221 A | 10/1986 |
| JP | H01237610 A | 9/1989 |
| JP | H05100201 A | 4/1993 |
| JP | H0728002 A | 1/1995 |
| JP | H08508826 A | 9/1996 |
| JP | H11352445 A | 12/1999 |
| JP | 2000347154 A | 12/2000 |
| JP | 2003230590 A | 8/2003 |
| JP | 2007323062 A | 12/2007 |
| WO | 8505466 A1 | 12/1985 |
| WO | 8701931 A1 | 4/1987 |
| WO | 9201417 A1 | 2/1992 |
| WO | 9321010 A1 | 10/1993 |
| WO | 9418599 A1 | 8/1994 |
| WO | 9423334 A1 | 10/1994 |
| WO | 9427169 A1 | 11/1994 |
| WO | 9706751 A1 | 2/1997 |
| WO | 9748004 A1 | 12/1997 |
| WO | 9827863 A1 | 7/1998 |
| WO | 9927334 A1 | 6/1999 |
| WO | 0049452 A1 | 8/2000 |
| WO | 03007851 A1 | 1/2003 |
| WO | 03050472 A1 | 6/2003 |
| WO | 03068059 A2 | 8/2003 |
| WO | 2004008189 A1 | 1/2004 |
| WO | 2004015460 A2 | 2/2004 |
| WO | 2004015481 A1 | 2/2004 |
| WO | 2004034095 A2 | 4/2004 |
| WO | 2004072687 A2 | 8/2004 |
| WO | 2005033782 A2 | 4/2005 |
| WO | 2005088388 A1 | 9/2005 |
| WO | 2006050366 A2 | 5/2006 |

OTHER PUBLICATIONS

Search Report in Israel Application No.296003 dated May 30, 2023, 3 pages.
Anderson "Adaptive Optics: Liquid Crystals Lower the Cost of Adaptive Optics" Laser Focus World (Dec. 1999), 3 pages.
Bertsch et al., "The Sensing Contact Lens", Medical Device Technology (2006); 17: 19-21.
Bradley "Profile: Larry N. Thibos, PhD., and Donald T. Miller, PhD." Indian Journal of Optometry; 2:1 (Spring 1999), 1 page.
Davis "Computer Vision Syndrome—The Eyestrain Epidemic" Review of Optometry (Sep. 15, 1997), 5 pages.
Eggers et al., "Wireless Intra ocular Pressure Monitoring System Integrated in an Artificial Lens", Presented at the First Annual International IEEE-EMBS Special Topic Conference on Microtechnologies in Medicine & Biology, Lyon, France, Oct. 12-14, 2000; Paper 7: 466-469.
Exam Report No. 1, Australian Application No. 2008207990, dated Aug. 7, 2012, 3 pages.
Extended European Search Report dated Dec. 22, 2017 from European Application No. 17187443.1, 11 pages.
Eyecare Business (Oct. 1997), 76 pages.
Fifth Office Action in CN Application No. 201110405247.8 dated Oct. 5, 2015, 7 pages.
International Preliminary Report on Patentability for Application No. PCT/US2008/051649 dated Jul. 28, 2009.
International Search Report in International Application No. PCT/US08/51649 dated Jul. 7, 2008.
International Search Report in International Application No. PCT/US09/037544 dated May 20, 2009.
Invitation to Respond to Written Opinion for Singapore Application No. 2012002556 dated Jun. 26, 2014, 2 pages.
ISA/US, Search Report and Written Opinion for application PCT/US05/39101, dated Jul. 7, 2006.
Kowel et al "Focusing by electrical modulation of refraction in a liquid crystal cell" Applied Optics 23:2 (1984), 12 pages.
Lazarus "The Use of Yoked Base-Up and Base-In Prism for Reducing Eye Strain at the Computer" Journal of the American Optometric Association (1996), 4 pages.
Leonardi et al., "A Soft Contact Lens with a MEMS Strain Gage Embedded for Intraocular Pressure Monitoring", Transducers '03; The 12th International Conference on Solid Slate Sensors, Actuators and Microsyslems, Boston, Jun. 8-12, 2003; 3B2.5: 1043-1046.
Leonardi et al., "First Steps toward Noninvasive IOP—Monitoring with a Sensing Contact Lens", Investigative Ophthalmology & Visual Science (2004); 45(9): 3113-3117.
Miller et al. "Requirements for the segmented spatial light modulators for diffraction-limited imaging through aberrated eyes," G.D. Love, ed. Proceedings of the 2nd International Workshop on Adaptive Optics for Industry and Medicine, World Scientific, Singapore, 63-68 (Jul. 1999).
Naumov "Control Optimization of Spherical Modal Liquid Crystal Lenses", Optics Express 4:9; Optical Society of America (1999), 9 pages.
Naumov, A.F. "Liquid Crystal Adaptive Lenses with Modal Control" Optics Letters, 23:13 Optical Society of America (1998), 3 pages.
Notice of Allowance in Japanese. Application No. 2009-546572, dated Nov. 15, 2013, 6 pages.
Notice of Allowance in U.S. Appl. No. 12/017,858 dated Jul. 16, 2015, 5 pages.
Notice of Grant, Australian Application No. 2008207990, dated Dec. 19, 2013, 2 pages.
Notice to Grant Patent Right, Chinese Application No. 201110405247.8, dated Mar. 7, 2016, 2 pages (English).
Office Action dated Jan. 22, 2017, for Israeli Application No. 252136, with partial translation, 4 pages.
Office Action in Canadian Application No. 2,675,772 dated Oct. 26, 2016, 5 pages.
Office Action in Indian Application No. 4873/DELNP/2009, dated Aug. 16, 2016, 8 pages.
Office Action in U.S. Appl. No. 12/017,858 dated Aug. 13, 2012, 11 pages.
Office Action in U.S. Appl. No. 12/017,858 dated Aug. 4, 2010, 13 pages.
Office Action in U.S. Appl. No. 12/017,858 dated Dec. 9, 2011, 12 pages.
Office Action in U.S. Appl. No. 12/017,858 dated Jan. 22, 2010, 8 pages.
Office Action in U.S. Appl. No. 12/017,858 dated Jun. 6, 2014, 14 pages.
Office Action in U.S. Appl. No. 12/017,858 dated May 21, 2015, 8 pages.
Office Action in U.S. Appl. No. 12/017,858 dated Oct. 23, 2014, 13 pages.
Office Action—Final Rejection in Korean AppIn 10-2009-7015395, dated Apr. 23, 2014, 5 pages.
Optics, Org, Dec. 19, 2006 "Liquid Lenses Eye Commercial Breakthrough" Opto & Laser Europe (Nov. 2003) 4 pages.
Pitchon, E.M. et al., "First In-Vivo Human Monitoring of Intraocular Pressure Fluctuation and Ocular Pulsation by a Wireless Soft Contact Lens Sensor." Congress of the European Glaucoma Society, Berlin, Jun. 2008; Congres annuel de la Societe francaise d'ophtalmologie, Paris, May 2008; ARVO Meeting (The Association for Research in Vision and Ophthalmology), Apr. 27-May 1, 2008, Fort Lauderdale American Glaucoma Society, 18th Annual Meeting, Mar. 2008, Washington, 1 page.
Restriction Requirement in U.S. Appl. No. 12/017,858 dated Aug. 24, 2009, 7 pages.
Supplementary European Search Report of Application No. EP 05824718 dated Nov. 19, 2007.
Supplementary Search Report for European Application No. 08713890 dated Aug. 6, 2012.
Tarascon et al., "Issues and challenges facing rechargeable lithium batteries" Nature 2001, 414:359-367 (Nov. 15, 2001).
Thibos et al., "Vision through a liquid-crystal spatial light modulator" Adaptive Optics Conference; Durham, UK, 1999, 6 pages.

(56) References Cited

OTHER PUBLICATIONS

Thibos et al., "Electronic Spectacles for the 21 Century" Indian Journal of Optometry, 2:1, 1999, 5 pages.
Thibos et al., "Use of Liquid Crystal Adaptive-Optice to Alter the Refractive State of the Eye; Optometry and Vision Science" 74:7; American Academy of Optometry (1997), 7pages.
Walter, P. et al., "Development of a completely encapsulated intraocular pressure sensor", Ophthalmic Research (2000); 32: 278-284.

* cited by examiner

Section "AA"

Section "AA"

FLEXIBLE ELECTRO-ACTIVE LENS

CROSS REFERENCE TO RELATED APPLICATIONS

This application is a continuation of U.S. application Ser. No. 17/938,070, filed Oct. 5, 2022, which is a divisional of U.S. application Ser. No. 16/159,289, filed Oct. 12, 2018, which is a divisional of U.S. application Ser. No. 14/850,232, filed Sep. 10, 2015, which is a continuation of U.S. application Ser. No. 12/017,858, filed Jan. 22, 2008, which claims priority to U.S. Provisional Application No. 60/881,514, filed Jan. 22, 2007, and to U.S. Provisional Application No. 60/960,607, filed Oct. 5, 2007; all of which are incorporated herein by reference in their entireties. This application is also related to U.S. Publication No. US 2006/0095128-A1, published May 4, 2006; U.S. Provisional Application No. 60/636,490, filed Dec. 17, 2004; U.S. Provisional Application No. 60/623,947, filed Nov. 2, 2004; U.S. Provisional Application No. 60/659,431, filed Mar. 9, 2005; U.S. Provisional Application No. 60/669,403, filed Apr. 8, 2005; and U.S. Provisional Application No. 60/960,607, filed Oct. 5, 2007; all of which are incorporated herein by reference in their entirety.

BACKGROUND

Intraocular lenses (IOLs) may be used within the surface of an eye for restoring vision function, for example, via implant for patients of cataract surgery, IOLs include monofocal lenses, which provide a single focus or single optical power, multifocal lenses, which provide multiple focus or optical power, and accommodating lenses, which adjust the focus of a lens.

The IOL may be inserted in a folded state through a small 3 mm or less incision of the eye. A syringe-like device having a piston may be used to help apply and position the IOL into the capsular bag which previously housed the removed natural crystalline lens. Once in the eye, the IOL maybe unfolded to its natural state. When the incision size for inserting an IOL into the eye is larger than 2-3 mm undesired astigmatic changes of the cornea occur. Therefore ophthalmologists prefer to use the smallest incision possible for inserting an IOL into the eye. Therefore this makes a flexible and foldable IOL practically a necessity.

Corneal inlays, corneal on-lays and single vision and bifocal contact lenses are also used to correct vision of the patient. In many cases these are worn to correct for the patients distance and near vision needs. Each of these is a very thin optic and requires curvature when applied on or in the eye.

Presently all known electro-active elements within an electro-active lens are made of rigid materials. In a certain previous embodiment of the inventors with regards to an electro-active contact lens an electro-active element is housed within a flexible outer host material. However, the electro-active element is rigid and therefore may add some thickness to the contact lens.

SUMMARY OF THE INVENTION

Embodiments of the invention provide a flexible electro-active lens including a flexible refractive optic having a fixed refractive index, an electro-active element embedded within the flexible refractive optic, wherein the electro-active element has an alterable refractive index, and a controller electrically connected to the electro-active element wherein when power is applied thereto the refractive index of the electro-active element is altered. The flexible electro-active lens may include one or more intraocular lenses, intraocular optics, spectacle lenses, contact lenses, corneal onlays, corneal inlays, and inter-ocular lenses.

DESCRIPTION OF THE DRAWINGS

A specific embodiment of the present invention will be described with reference to the following drawings, wherein.

The method and apparatus of the present invention will be better understood by reference to the following detailed description of specific embodiments and the attached figures which exemplify such embodiments.

DETAILED DESCRIPTION OF SPECIFIC EMBODIMENTS

The following preferred embodiments as exemplified by the drawings is illustrative of the invention and is not intended to limit the invention as encompassed by the claims of this application.

A flexible electro-active lens 2 is illustrated in FIG. 1, FIG. 2A, FIG. 2B, FIG. 3A, FIG. 3B, FIG. 4A, FIG. 4B, FIG. 5A, FIG. 5B, FIG. 5C, FIG. 5D, FIG. 7A, and FIG. 7B according to different embodiments of the present invention. Although the electro-active lens is described, embodiments of the invention may be used as other lenses including, for example, intraocular lenses, spectacle lenses, contact lenses, corneal onlays, corneal inlays, and inter-ocular lenses.

The electro-active element (e.g., described in reference to FIG. 1, FIG. 2A, FIG. 2B, FIG. 4A, FIG. 4B, FIG. 5A, FIG. 5B, FIG. 5C, FIG. 5D, FIGS. 7A, and 7B), the liquid crystal layer (e.g., described in reference to FIG. 4A and FIG. 4B), and a pixilated element may all be used to describe materials having optical properties that may be altered by electrical control. Although the alterable properties described herein typically include refractive index and optical power, embodiments of the invention may include electro-active lens 2 having other alterable properties, such as for example, prismatic power, tinting, and opacity. The properties of the materials may be controlled electrically and/or optically.

Terms such as "rigid", "hard", "inflexible", "inelastic" and/or "not foldable", may all be used to describe a material or structure adapted for resisting structural or shape changes when a force above a predetermined threshold is applied. Terms such as "bendable", "soft", "flexible", "elastic", and/or "foldable", may all be used to describe a material or structure adapted for changing structure or shape when a force above the predetermined threshold is applied. Terms such as "unfolded", "unfolded state", "natural", "flat", and/or "relaxed", may all be used to describe a material or structure in a relatively high entropy state (e.g., as shown in FIG. 2B, FIG. 3A, FIG. 3B, FIG. 4B, FIG. 5A, FIG. 5B, FIG. 5C, FIG. 5D, FIG. 7A, and FIG. 7B). Terms such as "folded", "folded state", "curved", and/or "bended", may all be used to describe a material or structure in a relatively low entropy state (e.g., as shown in FIG. 1, FIG. 2A, and FIG. 4A).

Figure 1:
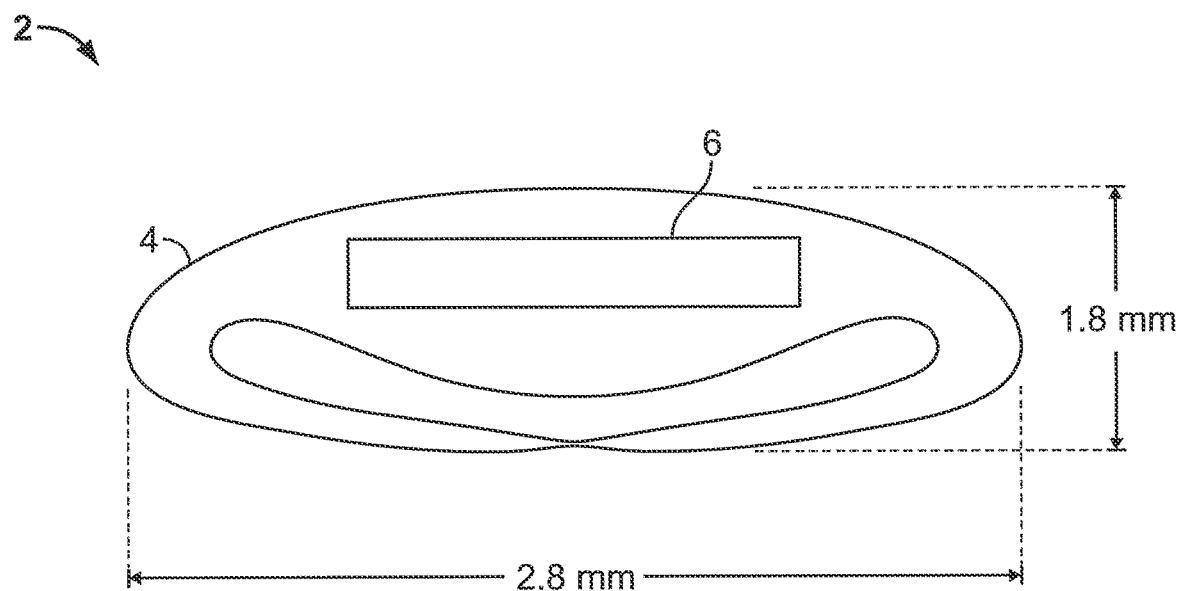
FIG. 1 shows a flexible electro-active lens 2 in a folded state having a flexible housing and an rigid electro-active element in accordance with an embodiment of the invention.

FIG. 1 shows a flexible electro-active lens 2 in a folded state having a flexible housing 4 and a rigid electro-active element embedded in the housing. The rigid electro-active element 6 typically does not bend when the electro-active lens is folded. The rigid element may protect elements contained therein from compression, bending due to expansion or contraction of materials, or other forces internal or external to the element. The rigid element may include a rigid encasing and may have elastic components, such as electro-active material. Typically the rigid element may be spaced from the peripheral edge of the electro-active lens to allow the folding thereof.

Figure 2A:
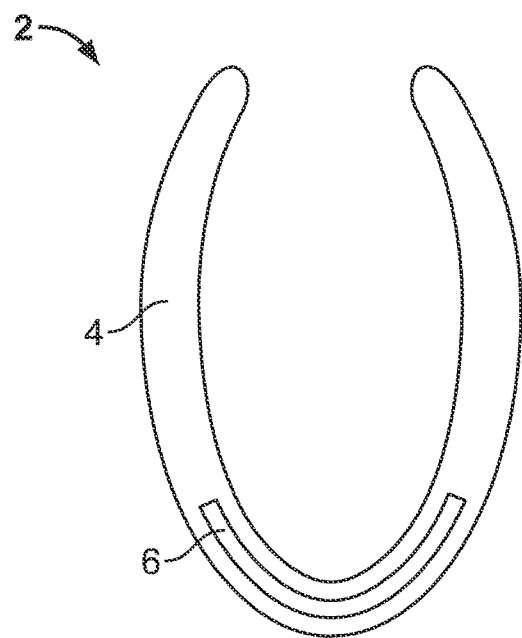
FIG. 2A shows a flexible electro-active lens 2 in a folded state having a flexible housing and a flexible electro-active element in accordance with an embodiment of the invention.

FIG. 2A shows a flexible electro-active lens 2 in a folded state having a flexible housing 4 and a flexible electro-active element 6 embedded in the housing. Since the flexible electro-active element typically does not prevent the electro-active lens from bending, the electro-active element may extend radially further toward the peripheral edge of the electro-active lens where the folding typically occurs. For example, when the electro-active lens is folded, the flexible electro-active element may curve along the peripheral bend of the folded lens. The flexible electro-active lens may be embedded in a rigid housing for use as a spectacle lens.

Figure 2B:
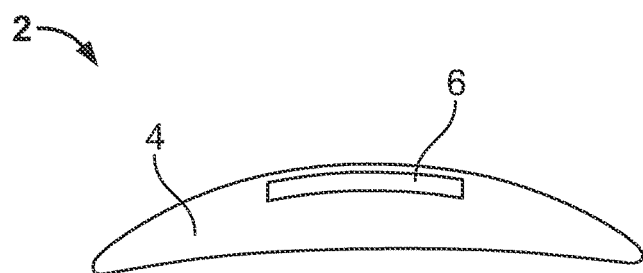
FIG. 2B shows an electro-active lens 2 in an unfolded state having a rigid housing and a flexible electro-active element in accordance with an embodiment of the invention.

FIG. 2B shows an electro-active lens 2 in an unfolded state having a rigid housing 4 and a flexible electro-active element 6 embedded in the housing. For example, the element may be minimally rigid for protecting elements contained therein from some internal or external forces and/or for biasing the electro-active lens toward the unfolded state. The electro-active element may be less flexible than the electro-active lens.

In reference to the flexible housing 4 in FIG. 1 and FIG. 2A, and in reference to the flexible electro-active element 6 in FIG. 2A and FIG. 2B, each of the flexible elements of the electro-active lens 2 may be adapted for moving between a folded state and an unfolded state. Each of the flexible housing and/or the flexible electro-active may be composed of a flexible material, such as, for example, polysulphones, polyetherimides, and/or other thermo-plastic materials. Polysulphones are a class of transparent dielectric polymers that are stable over a wide temperature range (e.g., from −110° C. to +150° C.) and pH range (e.g., from 2 to 13). Polysulphones are highly resistant to mineral acids, alkali, electrolytes, acids, and bases. Polysulphones are highly resistant to oxidizing agents such as bleaches, which, when for example, the electro-active lens is used as a contact lens, may be applied to the flexible housing for lens cleaning.

Referring again to FIG. 1, FIG. 2A, and FIG. 2B, the housing may or may not have optical power. A housing with optical power may have a fixed optical power and may be a refractive or diffractive lens (e.g., shown in FIG. 3A and FIG. 3B). For example, a housing without optical power may not focus light.

The electro-active element 6 may have an alterable refractive index. The electro-active element may be disposed between electrodes (e.g. shown in FIG. 3A, FIG. 3B, FIG. 5C, and FIG. 5D), which may be adapted for applying power to the element. The electro-active lens 2 may include a controller (e.g. shown in FIG. 3A, FIG. 3B, FIG. 5C, and FIG. 5D), which may be electrically connected to the electro-active element, for example, via the electrodes. The controller may be adapted for electrically driving the electrodes for modulating the power applied to the electro-active element. When power is applied to the element, for example, above a predetermined threshold, the refractive index thereof is altered. The controller may include drive electronics, a power supply such as a rechargeable battery, and other elements for driving the electrodes.

Referring again to FIG. 2A, the electro-active lens 2 may be a flexible electro-active lens including a flexible housing 4 and a flexible electro-active element 6 embedded in the housing. The flexible housing may have a fixed optical power. The electro-active element may have an optical power adapted for changing within an optical power range of from a minimum optical power to a maximum optical power. Electrodes 10 may be electrically connected to the electro-active element for applying power thereto. When power is applied to the element below a first predetermined threshold, the element may have the minimum optical power. When power is applied to the element above a second predetermined threshold, the element may have the maximum optical power. The fixed optical power may be greater than the maximum optical power. In this way, the fixed optical power may provide the majority of the optical power of the flexible electro-active lens.

In the present invention, for failsafe operation, when no power is applied (e.g., across the electrodes), the loss in optical power provided by the electro-active element may be minimal. For example, the lens 2 may function as a static lens having a fixed optical power, for example, adapted for correcting at either far, or alternatively at intermediate distance, or alternatively at near distance.

Figure 3A:
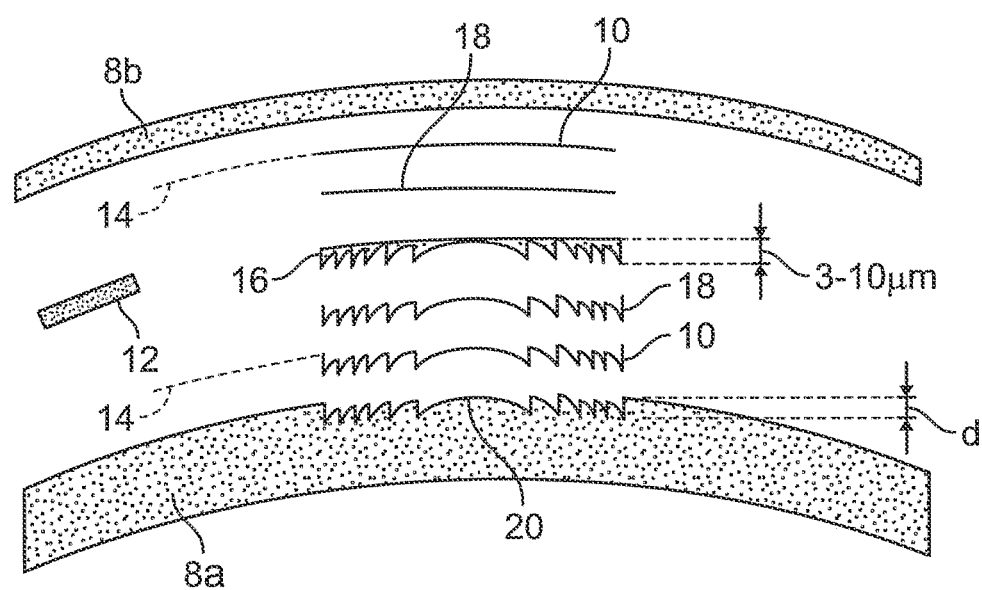
FIG. 3A and FIG. 3B show an expanded and collapsed view, respectively, of a flexible electro-active lens 2 in an unfolded state having a surface relief diffractive pattern and a liquid crystal layer in accordance with an embodiment of the invention.
Figure 3B:
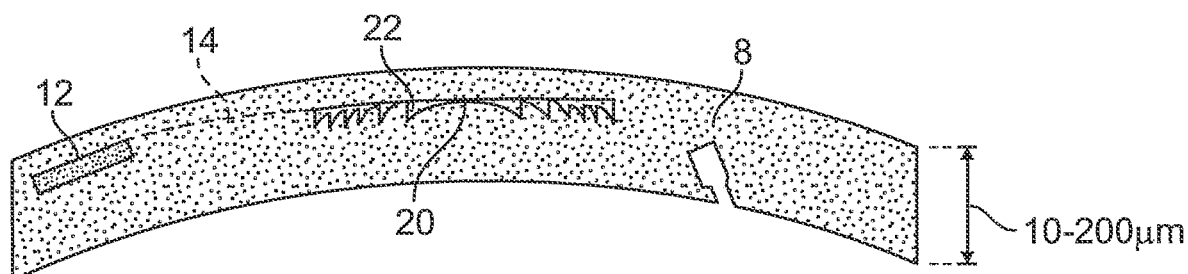
Figure 4A:
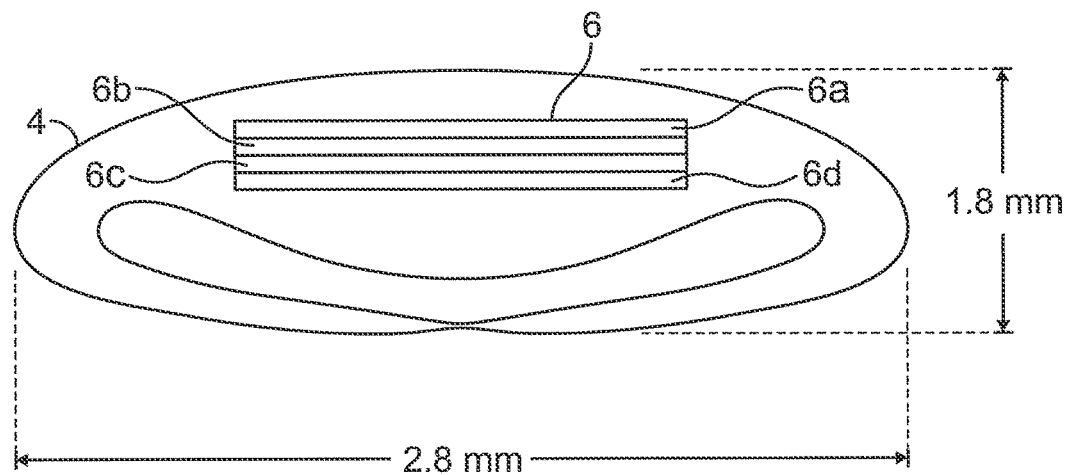
FIG. 4A shows the flexible electro-active lens 2 in a folded state having a plurality of electro-active elements in accordance with an embodiment of the invention.

Referring to FIG. 1, FIG. 2A, FIG. 2B, FIG. 3A, and FIG. 3B, the housing 4 may include an anterior film and a posterior film for containing the electro-active element. For example, each of the films may be approximately 100 microns thick and the electro-active lens may be approximately less than or equal to 500 microns thick. Referring to FIG. 2A and FIG. 3B the electro-active lens may be, for example, approximately less than or equal to 200 microns thick in the unfolded state. The unfolded electro-active lens may be, for example, approximately 9 mm wide and the folded electro-active lens may be for example less than or equal to approximately 3 mm wide.

When used as a corneal inlay, the diameter of the electro-active lens should not exceed the diameter of the cornea. In some embodiments of the invention, the outer surface of the housing may be curved to substantially match the curvature of the cornea (when used in a corneal inlay) or the surface of the eye (when used in a contact lens).

FIG. 1 includes an example of the measures of a folded electro-active lens 2 in two dimensions. The horizontal dimension of a folded electro-active lens is preferable less than or equal to 2.8 mm, although other dimensions may be used.

Figure 4B:
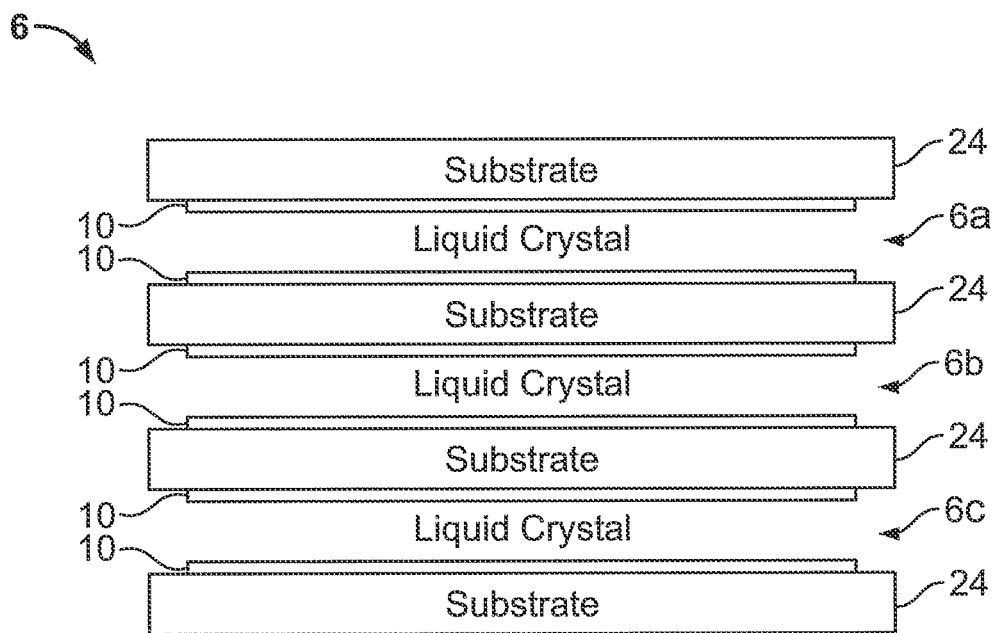
FIG. 4B shows the plurality of electro-active elements of FIG. 4A in accordance with an embodiment of the invention.

Referring to FIG. 4A and FIG. 4B, the electro-active element may include multiple individually activated liquid crystal layers for providing additional optical powers between the minimum and maximum optical powers.

FIG. 3A and FIG. 3B show an expanded and collapsed view, respectively, of a flexible electro-active lens 2 in an unfolded state having a surface relief diffractive pattern and a liquid crystal layer in accordance with another embodiment of the invention. The electro-active lens may be a flexible lens including a first flexible film 8a having a surface relief diffractive pattern 20 that varies within a depth, d, a second flexible film 8b, a liquid crystal layer 22 having electro-active material 16, electrodes 10, a controller 12, electrical connections 14, and alignment layers 18. The liquid crystal layer may be disposed between the first and second films, which may form a flexible housing 8 for encasing the layer. The films may be composed of, for example, polysulphones, polyetherimides, and/or other flexible materials.

The electrodes 10 may be electrically connected to the liquid crystal layer for applying power thereto. The controller 12 may be adapted for electrically driving the electrodes for modulating the power applied to the layer. The liquid crystal layer may have an alterable refractive index. When power is applied to the layer, for example, above a predetermined threshold, the refractive index thereof is altered.

The alignment layers 18 may orient the molecules of electro-active material 16 for providing an initial refractive index of the liquid crystal layer 22 when power below a first predetermined threshold is applied thereto. An electric field having power above a second predetermined threshold may be applied (e.g., across the electrode) for aligning molecules of electro-active material for altering the refractive index of the liquid crystal layer.

The refractive index of the first and second films is typically fixed. In one example, the refractive index of the liquid crystal layer may alternate between matching and mismatching the fixed refractive index of the first and second films.

In FIG. 3A and FIG. 3B, for failsafe operation, when no power is applied (e.g., across the electrodes), the liquid crystal layer may have (by way of example only) a refractive index, n, (e.g., 1.67 and a thickness (e.g., less than 10 ?m) approximately equal to the surface relief diffractive pattern 20 of the film. In this embodiment the material making up the surface relief diffractive also has a 1.67 index. When the refractive index of the liquid crystal layer matches the refractive index of the surface relief diffractive the electro-active lens will have a negligible optical power. When the index of the liquid crystal does not match that of the diffractive material the electro-active lens will have an optical power as that created by the diffractive pattern.

FIG. 4A shows the flexible electro-active lens 2 in a folded state having a plurality electro-active layers and FIG. 4B shows the plurality of electro-active elements of FIG. 4A. In FIG. 4A, the electro-active lens may include a flexible housing 4 having a fixed refractive index, a plurality of electro-active elements 6a, 6b, 6c, and 6d embedded therein, for example, arranged in a stacked configuration, and electrodes 10 independently electrically connected to each of the electro-active elements. In FIG. 4B, the electro-active elements 6a, 6b, and 6c may include layers of electro-active material 16 separated by an insulatory material 24, such as, a flexible dielectric film. In FIG. 4A and FIG. 4B the electro-active elements may be rigid, flexible, or less flexible than the housing.

In FIG. 4A and FIG. 4B each of the electro-active elements may have an alterable refractive index and may be individually activated. Since each electro-active element is insulated from one another it is possible to selectively or in any combination turn on an electro-active element or elements. By doing this it is possible to have an additive combination of optical powers or provide for a single optical power. This allows for the ability to tune the optical power of the lens or optic comprising such an optically stacked multiple layer of electro-active elements post surgical implantation.

The electro-active elements may be activated in response to a control signal from a source external to the electro-active lens. Referring to FIG. 5A, FIG. 5B, FIG. 5C, and FIG. 5D, the electro-active lens may include a receiver, such as, sensing device and/or a memory metal, for receive control signals from a source external to the lens. The control signals may be used to modulate the power applied to each of the elements for remotely tuning the optical power thereof.

Referring again to FIG. 4A and FIG. 4B, the electro-active elements may be stacked and may be individually activated for altering the total optical power of the electro-active lens in any combination of the alterable optical powers of the elements.

In FIG. 4B the electro-active lens includes electro-active elements 6a, 6b, and 6c that, when activated, have exemplary optical powers of +0.25 D or −0.25 D, +0.50 D or −0.50 D, and +2.50 D or +1.25 D, respectively. For example, the elements may be activated in various combinations for providing a total optical power in a range of from a minimum optical power of +0.25 D or −0.25 D by way of example only, by activating only a +0.25 D or and a −0.25 D which ever is needed to a maximum optical power of +4.50 D by way of example only, by activating a combination of a +25 D, a +50 D, a +2.50 D, and a +1.25 D. In this example, the electro-active lens may have optical powers in each increment of 0.25 D (positive or negative) between the minimum and maximum powers. When each of the elements is individually activated in suitable combinations, the element may provide an increment of change in optical power and the total optical power of the electro-active lens may be tuned to desired optical powers. The increment of change in optical power in this example is 0.25 D, but in certain other embodiments it is 0.12 D. The elements may be adapted for providing correction for near, intermediate, and/or far distance viewing. It may be appreciated that the values used herein are intended for demonstration and different optical powers, increments of change in optical power, and/or numbers of the electro-active elements (e.g., limited in site for fitting the eye) may be used.

In the present invention, one or more of the elements 6c may be pixilated. The electrodes may apply power to the pixilated elements. By shunting certain electrodes it is possible to provide approximately 50% of the maximum optical power of the elements. In the example above, element 6c may provide a maximum optical power of +2.50 D and a 50% reduced optical power of +1.25 D.

One or more of the electro-active elements may comprise a modal element. Modal elements may change optical power when an electrical potential gradient is applied to a variable focus modal lens. Modal elements can create a refractive optic using, for example, liquid crystal.

Referring again to FIG. 4A and FIG. 4B, the electro-active elements 6a, 6b, 6c, and 6d may include a combination of polymer dispersed liquid crystals and bi-stable liquid crystals. When sufficient power is applied to each of the elements (e.g., across the electrodes) the bi-stable crystals may be tuned for achieving a desired optical power while the polymer dispersed liquid crystals may be remotely cured or fixed within the element once the desired optical power is set. Curing the crystals may fix the orientation of the molecules for securing the tuned optical power while the electro-active lens is positioned or embedded in the eye. An electro-magnetic signal (e.g., a laser) having an eye-safe wavelength(s) (e.g., 1.5 ?m wavelength) may be used for remotely curing the crystals, for example, using an initiator that is sensitive to the wavelength(s) of the electro-magnetic signal. Polymer dispersed liquid crystals may include, for example, a mixture of a nematic liquid crystal mixture E7 (produced by Merck) and a UV cured optical adhesive NOA65 (produced by Norland Products). In one embodiment, the bi-stable liquid crystal may be remotely tuned and the polymer may be remotely cured using devices positioned external to the eye, while the electro-active lens is embedded within the eye.

Bi-stable liquid crystal material may be used to reduce the amount of electrical power consumption required over time to power the electro-active lens. Upon application of an appropriate first voltage above a first predetermined threshold, the overall orientation of the each of the individual bi-stable liquid crystals may retain an orientation induced by the first voltage once the voltage is removed. They may be returned to their original state by applying a second voltage below a second predetermined threshold. Bi-stable liquid crystals may include, for example, surface stabilized ferroelectric liquid crystal (SSFLF), which is a smectic liquid crystal. The use of a bi-stable liquid crystal may reduce electrical power consumption, because voltage may be used to just switch the device between its states and typically not to maintain the states of operation.

FIG. 5A, FIG. 5B, FIG. 5C, and FIG. 5D, each show a front view of a flexible electro-active lens 2 having a flexible electro-active element 6. The flexible electro-active lens includes a flexible film 4 in which the electro-active element is embedded, a power source 26, electrodes 10 and a memory metal material 28. The memory metal material may bias the electro-active lens into its unfolded state. For example, the electro-active lens may be folded for inserting into an incision in the eye. Once the electro-active lens is released within the eye, the memory metal material may unfold the lens into its unfolded state for operation within the eye.

Figure 5A:
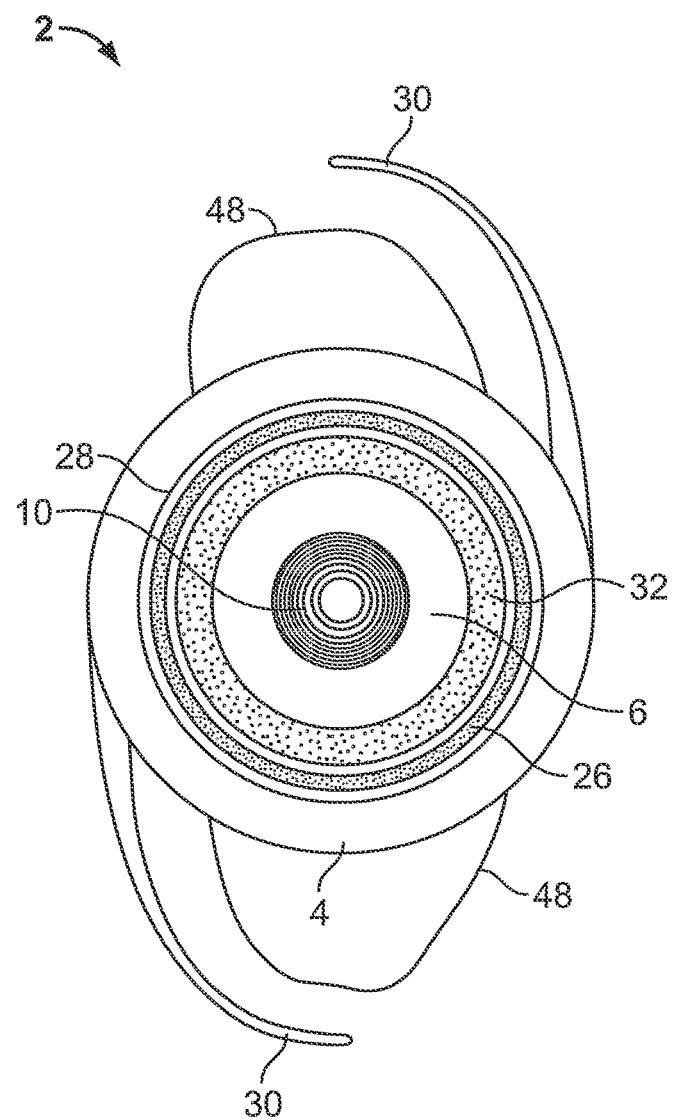
FIG. 5A, FIG. 5B, FIG. 5C, and FIG. 5D, each show a front view of the flexible electro-active lens 2 having an electro-active element, in accordance with an embodiment of the invention.
Figure 5B:
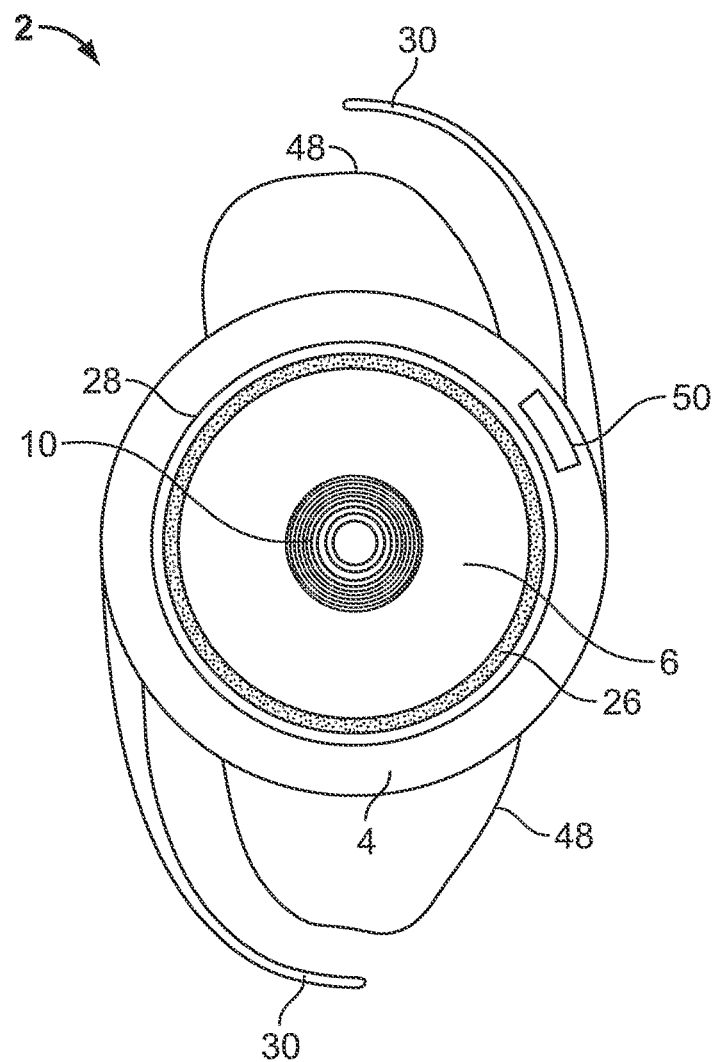
Figure 5C:
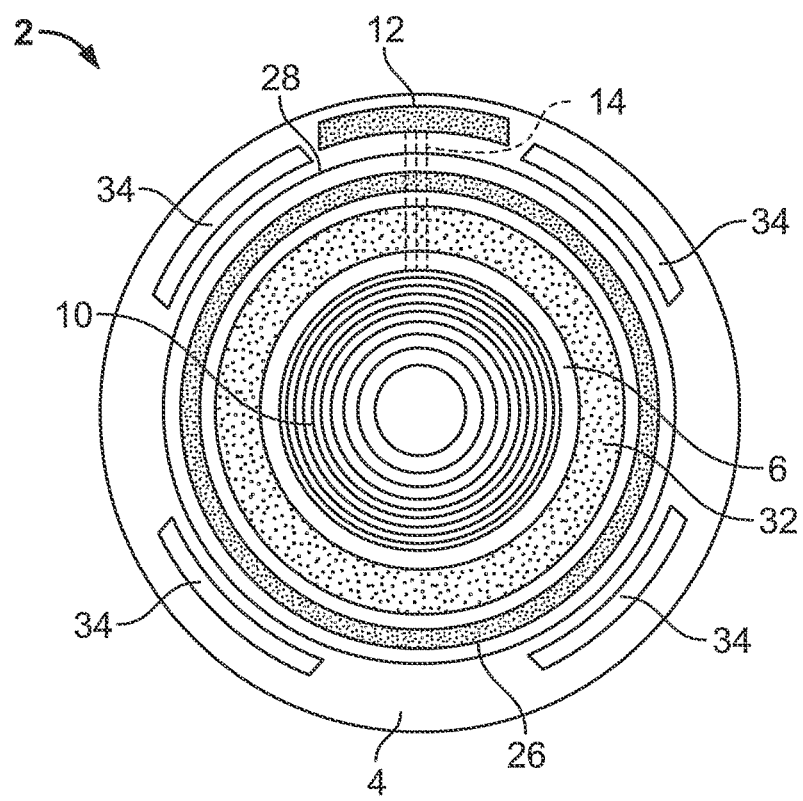
Figure 5D:
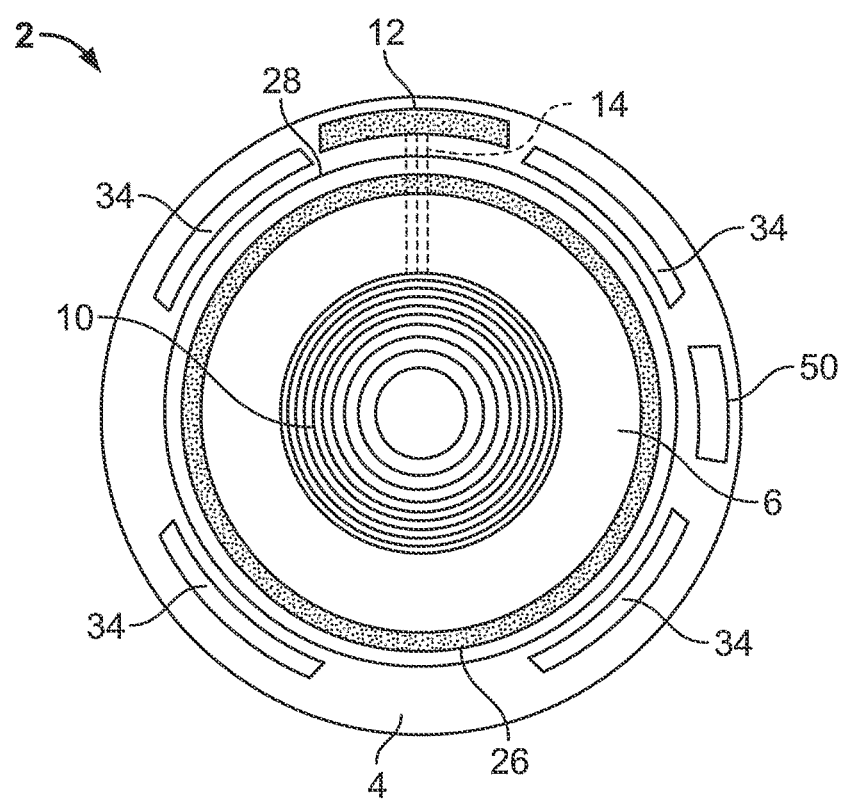

Referring to FIG. 5C and FIG. 5D, the electro-active-lens may include a controller and/or drive electronics 12 and electrical connections 14.

The electrodes 10 may be electrically connected to the electro-active element for applying power thereto. Referring to FIG. 3A, at least one of the electrodes may form a relief pattern, conforming to the surface relief diffractive pattern 20 of the first film 8a.

Referring again to FIG. 5A, FIG. 5B, FIG. 5C, and FIG. 5D, the electrodes may include a plurality of concentric electrode rings. When the electrodes apply electrical power to the electro-active element having such rings, the element may thereby be provided with diffractive optical properties.

In the present invention, the electrodes may be switched on and off in less than approximately one (1) second. The electrodes may be composed of a conductive or metal material such as aluminum, an optically transparent material, such as, indium tin oxide (ITO), a conductive organic material, such as, poly(3,4-ethylenedioxythiophene) poly (styrenesulfonate) (PEDOT:PSS) and/or carbon nano-tubes. The electrodes may coat and surround the liquid crystal material. The transparent material may include thin traces of metals such as silver or aluminum for increasing conductivity. Power may be applied across the transparent electrodes for altering optical properties of the electro-active lens, as described herein. The thickness of the electrode layer may be, for example, less than 1 ?m but is preferably less than 0.1 ?m. The controller and/or drive electronics 12, the power source 26, the memory metal material 28, and other electronic components may be connected to the electrodes by the electrical connections 14. The electrical connections may include small wires or traces, which may also be transparent. The electrodes and electrical connections may be flexible.

Referring to FIG. 5B and FIG. 5D, the electro-active lens may include a kinetic energy 50 electrically connected to the electro-active element for converting the motion of the eye into electrical power for providing the electro-active element with the electrical power. The kinetic energy driver may include a conductor and permanent magnets located within the driver. When the conductor moves relative to a magnetic field produced by the permanent magnets, electrical power is generated. Such drivers are well known in the art and are typically used for non-battery powered wrist watches. For example, eye movements such as rapid eye movements (REM) may charge the power source 26 (e.g., during sleep and/or wake cycles).

Referring to FIG. 5A and FIG. 5B, the electro-active lens may include piezo electric film 48 for generating electrical power. The piezo-electric film may be adapted for connecting the electro-active lens to an eye structure. The tension of the piezo-electric film may be changed by the motion of the eye. The film may transduce the change in tension into electrical power. For example, when the piezo-electric film may be attached to the ciliary body, iris, near or on the pupil, and as the pupil dilates and/or constricts the piezo-electric film would be stretched and relaxed, thereby producing electrical power.

Referring to FIG. 5A and FIG. 5C, the electrical power may be generated using a photovoltaic cell of sensing device 32. The photovoltaic cell converts solar power into electrical power as is known in the art. The photovoltaic cell may be adapted for charging using a 1.5 ?m infra-red laser source (not shown), for example, positioned external to the electro-active lens. The laser may, for example, be mounted on a pair of spectacles adapted to recharge the power source when worn by a user.

In each of these embodiments, the electrical power generated may be stored within the power source 26. The power source may include a battery, such as a thin film battery, which may be rechargeable and/or flexible. The thin film battery may be inductively charged by remote charging. In one embodiment a inductively enabled pillow (not shown) provides the inductive charge while the user of such an electro-active lens is sleeping.

In one embodiment, the memory metal material 28 may be used for biasing the electro-active lens toward the unfolded state.

In another embodiment, the memory metal material may be used for receiving control signals from a source external to the electro-active lens. The controller 12 may use the control signals for modulating power applied to the electro-active element. The memory metal material may be electrically connected to the controller and the electro-active element. For example, the memory metal material may function as an antenna, capacitor, inductive coil or the like.

In another embodiment, the memory metal material may be used for charging the power source 26. The memory material may form a coil and/or an antenna and may be adapted for inductively charging the power source using electrical power transmitted wirelessly from a device external to the electro-active lens.

In still another embodiment, the memory metal material may be used for programming and/or reprogramming the controller and/or drive electronics.

The memory metal material may be composed of, for example, titanium-palladium-nickel, nickel-titanium-copper, Gold-cadmium, Iron-zinc-copper-aluminum, Titanium-niobium-aluminum, hafnium-titanium-nickel, nickel-titanium-copper, gold-cadmium, iron-zinc-copper-aluminum, nickel-titanium, and/or iron-manganese-silicon, or any combination thereof.

Referring again to FIG. 5A and FIG. 5C, the electro-active lens may include a sensing device 32 for detecting sensory information. The sensing device may include for example one or more of the following devices: a photovoltaic or sensitive photo cell, a tilt switch, a light sensor, a passive range-finding device, a time-of-flight range finding device, an eye tracker, a view detector which detects where a user may be viewing, an accelerometer, a proximity switch, a physical switch, a manual override control, a capacitive switch which switches when a user touches the nose bridge or the like.

The sensing device may include two or more photodetector arrays with a focusing lens placed over each array for measuring distances. A sum of differences algorithm may be used to determine which array has the highest contrast ratio for determining the distance in which an object is placed from the electro-active lens.

The sensing device may include a range finder for detecting distances for focusing the electro-active lens and/or a solar cell for detecting light ambient and/or incident to the electro-active lens.

Figure 6:
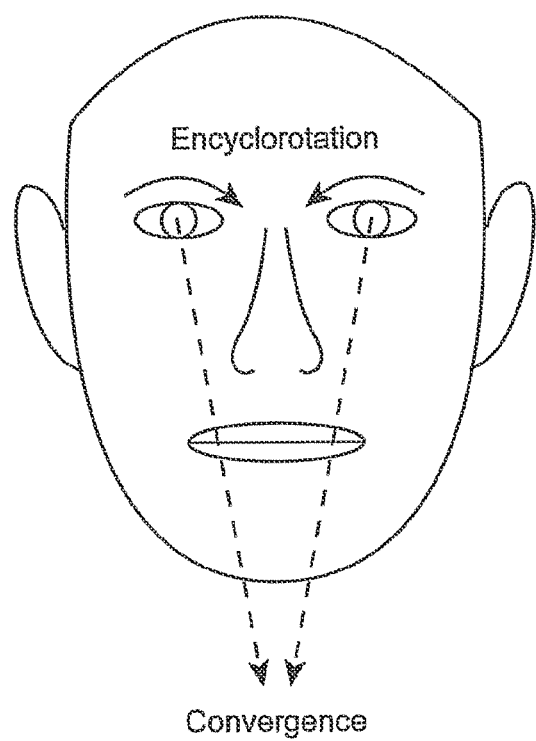
FIG. 6 shows encyclorotation of the eyes.

The sensing device may include a micro-electro-mechanical system (MEMS) gyroscope adapted for detecting head tilts or encyclorotation of the eye, an illustration of which is shown in FIG. 6. In addition, the sensing device may include a timing mechanism may be used in combination with the gyroscope for distinguishing a change in the distance viewed from the effects of bending over or other movements.

In response to the detection, the sensing device may trigger the activation and/or deactivation of one or more of the aforementioned elements of the electro-active lens, for example, by altering the electrical power applied thereto. The sensing device may be directly or indirectly coupled to the electronics and/or the electrical connections for electrically driving the electrodes. In one embodiment, the sensing device may detect the focusing distance at which a user is viewing and may alter or maintain the optical power of the electro-active element accordingly. In one example, if the sensing device detects that the user is focusing within the near distance range, the optical power of the element may be altered so that the electro-active lens provides correction for near distance viewing.

In the present invention, the electro-active lens may further include an over-riding remote switch (not shown) to manually over and switch optical states of the electro-active lens. For example, the remote switch may activate, deactivate, or set a desired optical power. When the remote switch is activated, a remote switch signal may be sent to the electro-active lens via an antenna formed from the memory metal material 28.

Referring again to FIG. 5C and FIG. 5D, the electro-active lens may include openings 34 for allowing nutrient and cellular waste products produced by the body to pass though the electro-active lens. The openings may be semi-permeable membranes that allow the passing of materials therethrough based on the size of the material molecules. The openings and/or pores may be drilled, machined, or stamped. Typically, the openings and pores may be located at non-electrical or otherwise non-critical areas of the electro-active lens such as near the pupillary axis where the electrodes do not extend or apply power. Such openings are well known in the art with regards to non-electro-active corneal inlays.

Figure 7A:
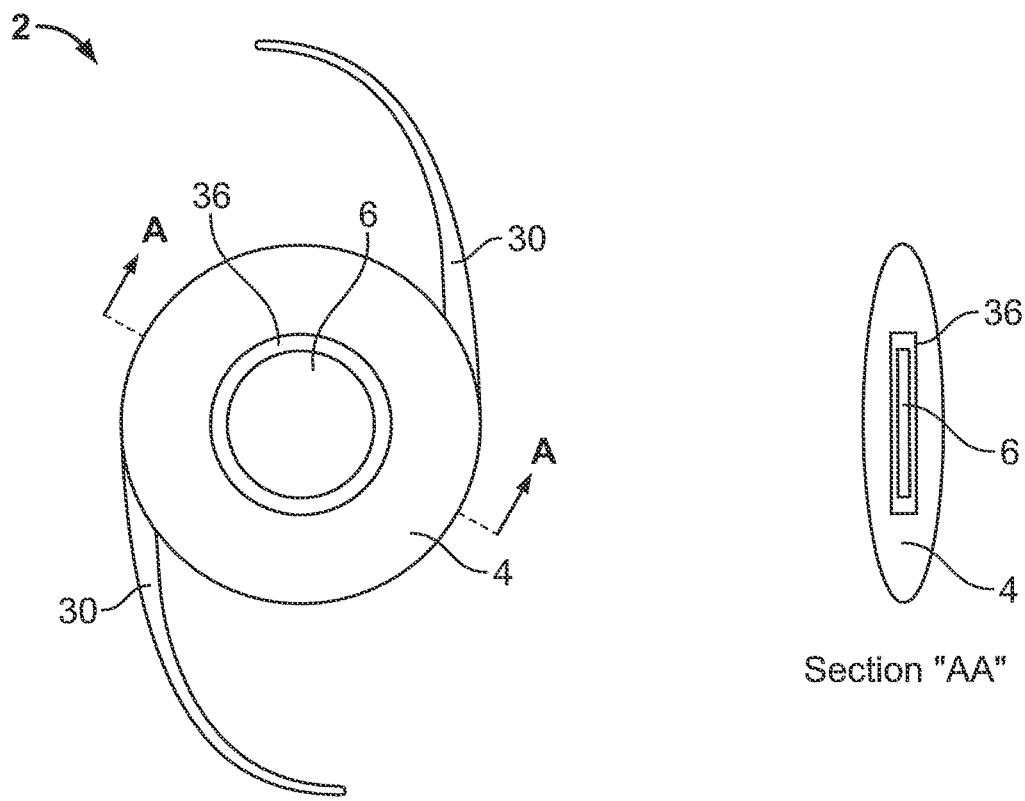
FIG. 7A and FIG. 7B each show a front view of the flexible electro-active lens 2 having an axis A and a cross sectional view of the flexible electro-active lens 2 taken at the axis A, in accordance with an embodiment of the invention.
Figure 7B:
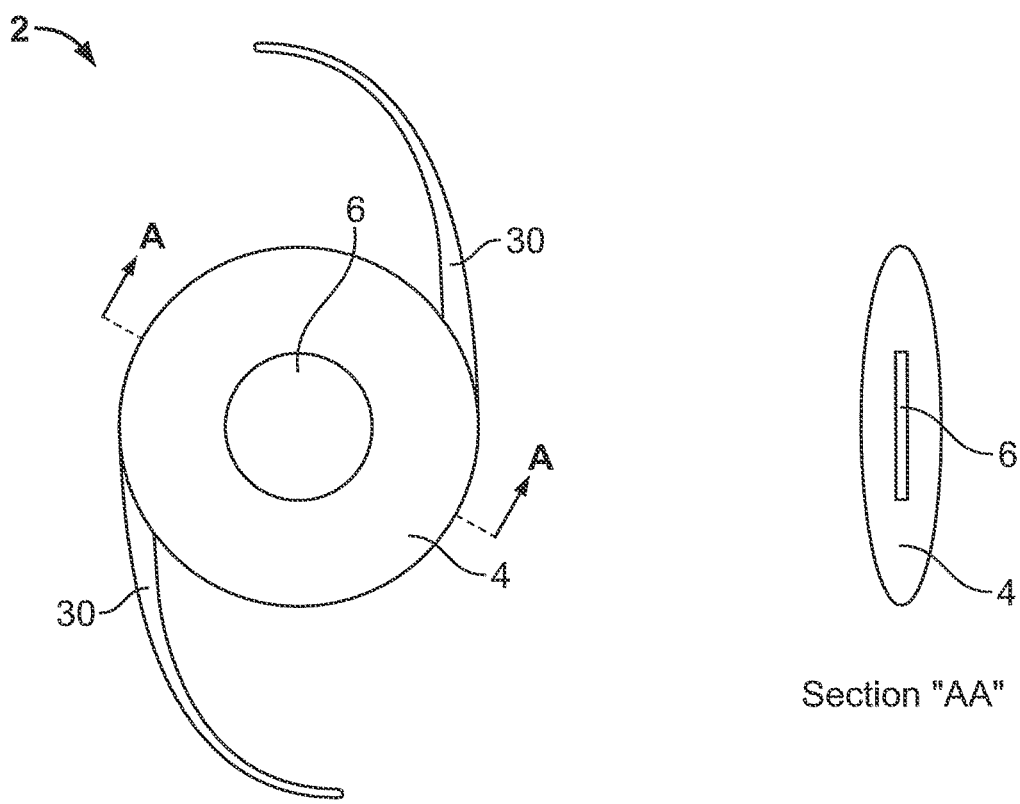

FIG. 7A and FIG. 7B each show a front view of the flexible electro-active lens 2 having an axis A and a cross sectional view AA of the flexible electro-active lens 2 taken at the axis A. The electro-active lens includes a flexible film 4 and an electro-active element 6 embedded in the film. FIG. 7A includes an envelope 36, disposed between the flexible film and the electro-active element. Thus, the element is surrounded by the envelope, which is in turn surrounded by the flexible housing. The envelope may be a water repellent, protective barrier composed of, for example, hydrophilic acrylic material. In one embodiment, the flexible housing may be composed of, for example, silicone or a hydrophobic acrylic material. Typically, hydrophilic acrylic materials have relatively low indices of refraction and are moderately rigid. Typically, hydrophobic acrylic materials have relatively higher indices of refraction and are flexible.

The housing 4 may be composed of a semi-permeable membrane. The housing may be coated with materials that are bio-compatible with anatomical objects in the eye. Bio-compatible materials may include, for example, polyvinyldene fluoride or non-hydrogel microporous perflouroether. The housing may optionally be coated with a sealer to prevent or retard the leaching of materials from the electro-active lens. The flexible housing 4 may be a semi-permeable substance. The liquid crystal electro-active element and the associated electronics may be hermetically sealed for preventing leaching out into the eye over time.

Referring again to FIG. 5A and FIG. 5B, the electro-active lens may include haptics 30 for stabilizing the lens in a desired location within the eye as is well known in the art. The haptics may also include an antenna and/or recharging loops for receiving control signals from a device external to the electro-active lens.

The electro-active lens may include intraocular lenses, which may be implanted with the greatest possible centration (an alignment of a center axis of the lens with a center axis or pupillary axis of the eye) to provide the best optical results. In a preferred embodiment of the present invention, the electro-active lens or a capsular bag housing the electro-active lens should be implanted directly behind the pupil with the greatest possible centration. The haptics 30 may be used to center the electro-active lens inside of the capsular bag. Alternately, the haptics may be attached directly to the eye, for example, the ciliary muscle, extending outside of the capsular bag. Because of anatomical asymmetry in the eye, the electro-active lens may be implanted decentral to a pupillary axis. Additional decentration may be found within the capsular bag (e.g., in a misalignment of a center axis of the capsular bag with a center axis of the electro-active lens inserted therein) and with a misaligned pupil (having a curve or misaligned pupillary axis). The eye is typically tolerant of moderate amounts of decentration. Due to anatomical asymmetry, a natural and unaltered eye may have approximately 0.1 or 0.2 mm of decentration. The electro-active lens may preferably accommodate at least 1 mm of decentration The electro-active lens may be implanted in an eye already having an existing lens implant for correcting optical dysfunction provided by the existing lens implant (not shown). This technique may be referred to as "piggyback" lens implantation. The electro-active lens may be implanted in front of the existing lens implant (e.g., closer to the exposed surface of the eye), for example, into the posterior chamber in the ciliary sulcus. In other embodiments, the electro-active lens may be implanted behind the existing lens implant (e.g., farther from the exposed surface of the eye). In any of the above embodiments, the electro-active lens may be used in combination with another, for example, fixed crystalline lens. The lens may be positioned in the anterior or posterior chamber of the ciliary sulcus.

When embodiments described herein are used as a contact lens, the lens may include an attached soft hydrophilic skirt at or near the lens periphery for stabilizing the lens in a desired centrated position. The contact lens may further be stabilized by having a weighted orienting region or a truncated attachment surface. The contact lens may be inductively charged by a contact lens case (not shown), for example, when the lens is located in the case. The sensing device 32 of the contact lens (e.g., a photo-detector) may be located in or on the surface of the contact lens or skirt attached, in a location spaced from the pupillary axis to not interfere with the vision of a wearer. In one embodiment, the dimensions fitting parameters and/or components may be customized according to the anatomical needs and/or preferences of a user.

Figure 8A:
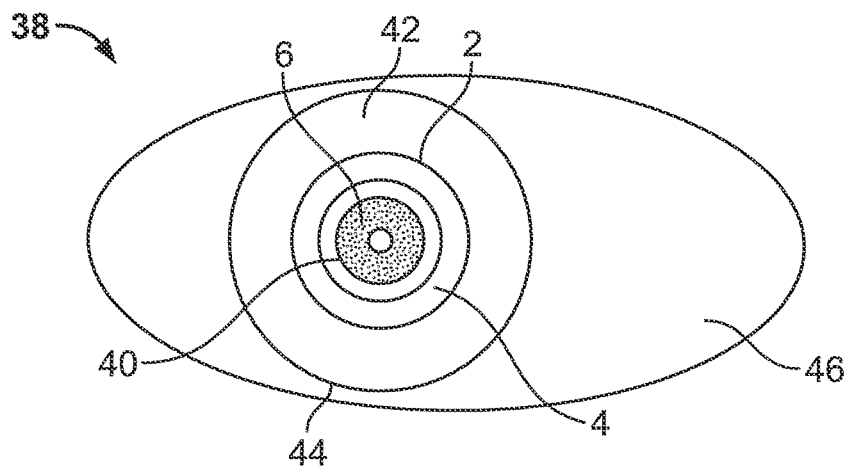
FIG. 8A, FIG. 8B, and FIG. 8C, each show the placement of the electro-active lens 2 in an eye having different pupil size, in accordance with an embodiment of the invention.
Figure 8B:
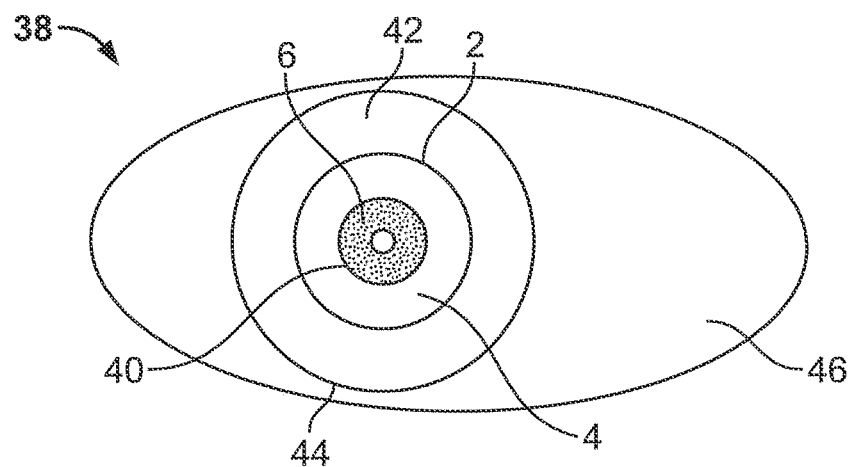
Figure 8C:
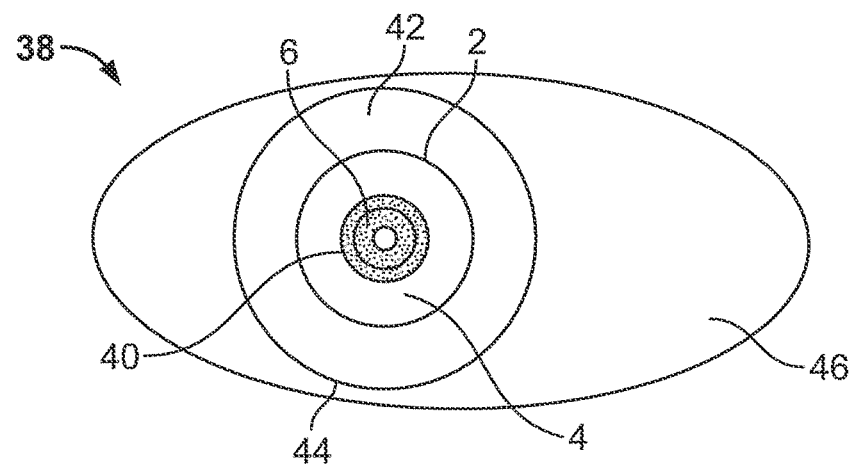

FIG. 8A, FIG. 8B, and FIG. 8C, each show the placement of the electro-active lens 2 in an eye 38 having different pupil sizes. FIG. 8A shows a dilated pupil having a relatively large size. FIG. 8B shows a pupil having a relatively moderate size. FIG. 8C shows a pupil having a relatively small size. FIG. 8A, FIG. 8B, and FIG. 8C, each show the relative locations of the pupil 40, the iris 42, the limbus 44, and the scelera 46, in the eye. The electro-active lens may include a flexible housing 4 and an electro-active element 6. As the size of the pupil decreased, the lens covers an increasing percentage of the pupil 40 or aperture of the eye.

In any of the above embodiments, liquid crystalline material may be used. Liquid crystals include a state of aggregation that is intermediate between the crystalline solid and the amorphous liquid. Many liquid crystals are composed of rod-like molecules, and classified broadly as: nematic, cholesteric, and smectic.

The electro-active lens may be used to correct refractive errors of the eye including, presbyopia, myopia, hyperopia, astigmatism, and higher-order aberrations.

When used herein, near viewing distance may describe distances from 18 inches up to approximately 12 inches from a view point; intermediate viewing distance may describe distances from greater than 18 inches to 29 inches and far viewing distance may describe distances greater than approximately 29 inches from ones face.

While the invention has been described with respect to a limited number of embodiments, it will be appreciated that many variations, modifications and other applications of the invention may be made. It will be appreciated by persons skilled in the art that the appended claims are intended to cover all such modifications and changes as fall within the true spirit of the invention.

The invention claimed is:

1. An energized ophthalmic lens device, comprising:
   a variable optic insert comprising at least a portion within an optical zone of the energized ophthalmic lens device and comprising a front curve piece and a back curve piece, wherein a back surface of the front curve piece and/or a front surface of the back curve piece have differing surface topology at least in the portion within the optical zone, the variable optic insert further comprising a non-optical zone;
   an energy source embedded in the variable optic insert in at least a region comprising the non-optical zone;
   a layer of liquid crystal material operatively associated with the variable optic insert; and
   a layer of dielectric material proximate to the layer of liquid crystal material, wherein the layer of dielectric material varies in thickness across a region within the optical zone resulting in a varying electric field across the layer of liquid crystal material when an electric potential is applied across the layer of liquid crystal material.

2. The energized ophthalmic lens device of claim 1 wherein the energized ophthalmic lens device comprises a contact lens.

3. The energized ophthalmic lens device of claim 2, further comprising:
   a first layer of electrode material proximate to the back surface of the front curve piece; and
   a second layer of electrode material proximate to the front surface of the back curve piece.

4. The energized ophthalmic lens device of claim 3, wherein the layer of liquid crystal material varies its index of refraction affecting a ray of light traversing the layer of liquid crystal material when an electric potential is applied across the first layer of electrode material and the second layer of electrode material.

5. The energized ophthalmic lens device of claim 4, wherein the variable optic insert alters a focal characteristic of the energized ophthalmic lens device.

6. The energized ophthalmic lens device of claim 5, further comprising a controller.

7. An ophthalmic lens device with a sealed variable optic insert positioned within at least a portion of an optical zone of the ophthalmic lens device, wherein the sealed variable optic insert comprises:
   a curved front surface and a curved back surface, wherein the curved front surface and the curved back surface are configured to bound at least a portion of a chamber;
   a dielectric layer proximate to at least one of the curved front surface and the curved back surface, wherein a thickness of the dielectric layer varies at least within the portion within the optical zone;
   an energy source embedded in the sealed variable optic insert in at least a region comprising a non-optical zone;
   a layer containing liquid crystal material positioned within the chamber,
   wherein the layer includes regions of liquid crystal material aligned by an alignment layer which orients molecules in the liquid crystal material; and
   wherein the curved front surface and the curved back surface have different radii.

8. The ophthalmic lens device of claim 7 wherein an optical effect of the layer containing liquid crystal material is supplemented by an effect of the thickness of the dielectric layer when an electric field is applied across the layer containing liquid crystal material.

9. The ophthalmic lens device of claim 8 wherein the ophthalmic lens device is a contact lens.

10. The ophthalmic lens device of claim 9 further comprising:
- a first layer of electrode material proximate to the curved back surface; and
- a second layer of electrode material proximate to the curved front surface.

11. The ophthalmic lens device of claim 10 wherein at least a portion of the layer containing liquid crystal material varies its index of refraction affecting a ray of light traversing the layer containing liquid crystal material when an electric potential is applied across the first layer of electrode material and the second layer of electrode material.

12. The ophthalmic lens device of claim 11 wherein the sealed variable optic insert alters a focal characteristic of the ophthalmic lens device.

13. The ophthalmic lens device of claim 12 further comprising an electrical circuit, wherein the electrical circuit controls a flow of electrical energy from the energy source to the first and second layers of electrode material.

14. The ophthalmic lens device of claim 13 wherein the electrical circuit comprises a processor.

\* \* \* \* \*